United States Patent
Molenaar et al.

(10) Patent No.: US 10,485,839 B2
(45) Date of Patent: Nov. 26, 2019

(54) APPLICATION OF GREEN TEA AND ITS DERIVATIVES, COMPOSITION FOR USE THEREWITH, VETERINARY PHARMACEUTICAL FORMULATION AND KIT OF PARTS

(71) Applicant: COOL-4-HORSES B.V., Bunnik (NL)

(72) Inventors: Johnny Franciscus Cornelis Molenaar, Dronten (NL); Mary Rose Elzinga, Dronten (NL)

(73) Assignee: COOL-4-HORSES B.V., Bunnik (NL)

( * ) Notice: Subject to any disclaimer, the term of this patent is extended or adjusted under 35 U.S.C. 154(b) by 0 days.

(21) Appl. No.: 15/483,746

(22) Filed: Apr. 10, 2017

(65) Prior Publication Data
US 2017/0209512 A1    Jul. 27, 2017

Related U.S. Application Data

(63) Continuation of application No. PCT/NL2015/050716, filed on Oct. 12, 2015.

(30) Foreign Application Priority Data

Oct. 10, 2014 (NL) ..................................... 2013605

(51) Int. Cl.
*A61K 36/82* (2006.01)
*A61K 31/353* (2006.01)
(Continued)

(52) U.S. Cl.
CPC ............ *A61K 36/82* (2013.01); *A61K 9/0017* (2013.01); *A61K 9/0053* (2013.01);
(Continued)

(58) Field of Classification Search
CPC .... A61K 36/82; A61K 31/353; A61K 9/0053; A61K 9/0017; A61K 36/38; A61K 36/185
See application file for complete search history.

(56) References Cited

U.S. PATENT DOCUMENTS

2002/0068099 A1   6/2002  Koniger
2002/0090402 A1   7/2002  Zhang

FOREIGN PATENT DOCUMENTS

WO    2016/056917    4/2016

OTHER PUBLICATIONS

Maeda-Yamamoto, et al., "The Efficacy of Early Treatment of Seasonal Allergic Rhinitis with Benifuuki Green Tea Containing O-methylated Catechin before Pollen Exposure: An Open Randomized Study", Allergology International, vol. 58, 2009, 437-444.
(Continued)

*Primary Examiner* — Trevor Love
(74) *Attorney, Agent, or Firm* — Peacock Law P.C.; Janeen Vilven (57) ABSTRACT

Use of a composition comprising the administration of crushed leaves of green tea in the treatment of type I allergy. The composition may especially be enriched with substances extracted from green tea, preferably catechin or a derivative thereof. The veterinary treatment of type I allergy, as in the treatment of sweet itch, is especially envisaged. A preferred embodiment comprises a composition for use according to the present invention, as well as a veterinary pharmaceutical formulation comprising a composition according to the invention, and a veterinary pharmaceutical formulation comprising said composition.

15 Claims, 5 Drawing Sheets

(51) Int. Cl.
*A61K 9/00* (2006.01)
*A61K 36/38* (2006.01)
*A61K 36/185* (2006.01)

(52) U.S. Cl.
CPC .......... *A61K 31/353* (2013.01); *A61K 36/185* (2013.01); *A61K 36/38* (2013.01)

(56) References Cited

OTHER PUBLICATIONS

Shiozaki, et al., "Effect of Tea Extracts, Catechin and Caffeine Against Type-I Allergic Reaction", Journal of the Pharmaceutical Society of Japan, vol. 117, No. 7, 1997, 448-454.

Van Den Boom, et al., "The Healing Effects of a Topical Phytogenic Ointment on Insect Bite Hypersensitivity Lesions in Horses", Tijdschrift voor Diergeneeskunde, vol. 136, No. 1, 2011, 20-26.

APPLICATION OF GREEN TEA AND ITS DERIVATIVES, COMPOSITION FOR USE THEREWITH, VETERINARY PHARMACEUTICAL FORMULATION AND KIT OF PARTS

CROSS-REFERENCE TO RELATED APPLICATIONS

This application is a continuation application of Patent Cooperation Treaty Application No. PCT/NL2015/050716, filed on Oct. 12, 2015, which claims priority to Netherlands Patent Application No. 2013605, filed on Oct. 10, 2014, and the specifications and claims thereof are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

COPYRIGHTED MATERIAL

Not Applicable.

BACKGROUND OF THE INVENTION

Field of the Invention (Technical Field)

The present invention relates to the use of green tea and active ingredients from green tea and derivatives thereof according to the preamble of claim 1. The invention especially relates to the veterinary use of same. The invention furthermore is directed to a pharmaceutical formulation and a nutritional supplement comprising green tea, for the treatment of type I allergy. The invention particularly relates to a preparation comprising catechin or an, optionally veterinary, active derivative thereof, for the treatment of type I allergy. Finally, the invention relates to a combination of components for the treatment of type I allergy.

Description of Related Art Including Information Disclosed Under 37 C.F.R. §§ 1.97 and 1.98

It is known that green tea has a high content of catechin. The term "high content" means that the content is higher than of other kinds of tea, such as black tea or white tea.

Catechin is in different forms available, whose mutual ratio being dependent of the kind of green tea. A characterizing example of a catechin is (−)-epigallocatechin-3-O-gallate, and its methylated form: (−)-epigallocatechin-3-O-(3-O-methyl)gallate.

The invention aims at green tea in general, and more in particular but not solely to catechin, especially its methylated form.

In practice it is known to administer catechin comprising preparations orally, in the form of green tea extracts. Research has shown in human subjects that some effect on type I allergic reactions can be obtained. Amongst others it has been shown that a long-term oral exposure of a few months, preceding exposing a subject to allergens, is required for obtaining an effect (Allergol. Int., 2009 September; 58(3); 437-449). Said effect, however, is very limited. Although the rate of allergic complaints diminished, did they not disappear completely.

BRIEF SUMMARY OF THE INVENTION

The present invention has as its object to solve the limitations of the prior art noted above.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

The present invention is directed to the use of a composition comprising the administration of crushed leaves of green tea, in the treatment of type I allergy. The invention especially also relates to such use wherein said composition comprises active ingredients from green tea and derivatives thereof, more in particular catechin.

Within the present invention, substantially use is made of the term "catechin", meaning "green tea, active ingredients from green tea and derivatives thereof, especially catechin". Where this description use is made of the term "catechin" said wider meaning is meant, unless is it unmistakably clear from the context that catechin itself or a derivative thereof is meant.

As a consequence, the invention also relates to a use wherein said composition is supplemented with substances extracted from green tea, preferably comprising catechin or a derivative thereof.

The invention is especially directed to the veterinary use of catechin. It has shown that especially sweet itch (SME), also known as summer eczema, caused by midges (Culicoïdes), can be treated very efficiently by means of the use according to the invention. The invention however, is not only limited to the use with horses. Other animals as well can be treated applying the use according to the invention for treatment and prevention of type I allergic reactions.

For that reason, the invention especially also aims at providing a composition, for example a pharmaceutical formulation or a nutritional supplement, for example a veterinary pharmaceutical formulation, for use in the treatment of type I allergic reactions, as in veterinary use for, for example, treatment of sweet itch. Such composition may comprise a combination of components (also identified as kit of parts).

In treatment of veterinary complaints like SME sometimes customized diets are applied, such as a low protein diet and a low starch diet. Treatment of the affected skin with sulfur containing ointments is applied as well. In some cases, even a treatment with corticosteroids is used for relieving complaints. However, it is virtually impossible to completely anoint a horse with corticosteroids and an oral treatment of a horse with corticosteroids may induce significant side effects. As a consequence, eventually, the only advise that can be given is to limit the rate of exposure to midges by providing the horses with a blanket, by keeping them in a stable or to house them in areas containing little midges (for example at coastal areas). Therefore, a satisfactory solution to this problem is not available, yet.

According to a further preferred embodiment the invention provides an improved use by administering the composition according to the invention topical. Administering the composition on the skin, especially on skin that has been damaged due to allergic reactions, a quick remarkable healing is obtained, to wit within a few days. Especially in acute treatment such use therefore is extremely useful. For that reason the composition according to the invention is preferred for use in a topical treatment.

According to an especially preferred embodiment the invention therefore relates to a use as mentioned above, comprising covering the skin that has been affected by sweet itch with crushed leaves of green tea.

More in particular a use is preferred comprising covering affected skin with a composition of crushed leaves of green tea and oil, said oil preferably being chosen from at least one of argan oil and tamanu oil. These kinds of oil have a naturally high content of catechin, which seems to add in the advantageous effects according to the present invention.

The term "high content" means that the content is higher than in other kinds of oil, like olive oil and coconut oil. However, kinds of oil other than argan oil and tamanu oil comprising a similar content of catechin can be used advantageously in the present invention as well.

It has furthermore shown that the use according to the present invention can advantageously be performed orally as well, providing an excellent result. The long term activity of the present invention especially is surprisingly good if the composition is regularly and repeatedly, preferably daily, administered orally. For example, healing of the affected skin due to type I allergic reactions starts very quickly, already within a few days. More in particular, a combined topical and oral use provide an excellent, quick and long lasting effect.

As a consequence, the invention furthermore and especially relates to such use comprising a daily administration of an oral dose of green tea in an amount in the range of from 0.05 to 1.0 gram per kg weight of the subject to be treated. Such provides an excellent recovery and healing of eczema affections that have already arisen.

More in particular a use is preferred comprising daily administering an oral dose of green tea in an amount in the range of from 0.1 to 0.75 gram per kg weight of the subject to be treated, more preferably in the range of from 0.1 to 0.5 gram green tea per kg of the subject to be treated.

Oral use also provides a long term effect wherein sensitivity to type I allergic reactions is substantially gone after a few months of oral administration of the composition according to the invention. It is remarked as well that in daily oral administration during two years in the midget season (April to October), in the subsequent season complaints about SME are diminished is during said subsequent season a weekly active dose of green tea is administered orally. Such is a completely surprising effect of the administration of green tea against type I allergic reactions.

The term "season" relates to the period of the year during which midgets are active, which is the period or periods that the temperature is above 15° C.

The invention especially relates to the use in veterinary oral treatment of a subject comprising the steps of: —administering during at least two months of a first season an amount of a substantially daily dose of green tea in an amount in the range of from 0.1 to 1.0 gram per kg weight of the subject to be treated, preferably during a time period wherein ambient temperature is above 15° C.; —administering during a second season an amount of a substantially daily dose of green tea in an amount in the range of from 0.1 to 1.0 gram per kg weight of the subject to be treated, preferably during a time period wherein ambient temperature is above 15° C. These steps provide an excellent recovery of eczema disorders that have already established and also provide a long term and lasting protection, even when the administration is stopped after some time. The administration during the first and second season is preferably performed during the complete period of time that the temperature is above 15° C., but in any case this period is at least 60% of that time, more preferably at least 75% of that time to obtain a long term-effect. Anyway, when performing the steps during a short period an excellent effect against acute type I allergic symptoms is obtained.

Preference is especially given to such use, further comprising: —administering during a subsequent third season, for every unit of time of 1 day to 14 days, an amount of an oral dose of green tea in an amount in the range of from 0.05 to 0.75 gram per kg weight of the subject to be treated, preferably during a time period wherein ambient temperature is above 15° C. Such administration of green tea during the subsequent third season, wherein said administration needs to take place only once every two weeks, provides a surprising effect in that the season thereafter the allergic reactions have virtually completely or even completely disappeared, even without further treatment according to the method according to the present invention. For example, exposure to midgets has no negative effect whatsoever for a horse if, during the three preceding seasons, it substantially completely underwent the use according to the invention and as mentioned above.

The term "substantially completely" means that the treatment was performed almost daily, as mentioned above. A short break is allowed, however, such break should be no longer than 4 weeks and preferably not more often than two times each season. The season usually is from April to October, but in any case when the maximum daytime temperature is above 15° C.

It is especially surprising that the method according to the invention provides the long term effects as have now been obtained. Although some in vitro tests have indicated the effectivity of green tea a in vivo has not been substantiated. A long term effect for type I-allergic reactions was completely unknown and could not be expected based on tests performed until now. Especially the curative effect of the administration according to the invention is a result that has not been shown in respect of type I-allergic reactions. This is a surprising effect that completely relieves sensitivity to type I-allergic reactions.

The use according to the invention can be performed in several ways for obtaining the efficiency. Especially preferred is a use wherein the composition comprises at least one of: [a] a dried extract of green tea leaves, that preferably comprises a high content of catechin, [b] a dried extract of green tea leaves in oil, that preferably comprises a high content of catechin, [c] crushed green tea leaves, and [d] crushed green tea leaves in oil. The crushed green tea leaves may be dried or not. Dried green tea leaves have the advantage that they can be preserved for a long time and, in combination with oil, easily deliver the active ingredients. The extracts may be used especially preferable for topical treatments. The crushed green tea leaves according to [c] may be administered to horses as solid food. Said dried extract of green tea leaves according to [a], that preferably comprises a high content of catechin, may for example be added to crushed green tea leaves, such that a mixture of crushed leaves with an enriched content of catechin is obtained. Such mixture, but also the dried extract according to [a] can preferably be admixed with solid food and be administered orally; the added catechin has a bitter taste that may be masked by other ingredients. As a matter of fact, a larger amount of crushed (and optionally dried) green tea leaves according to [c] may be administered orally, but such might lead to a too high content of caffeine, which is contained in tea leaves naturally, and which is considered as a stimulant. Especially for racing horses, it is preferred that no superfluous amounts of caffeine are administered.

Where crushed green tea leaves in oil are used for topical administration, it is preferred that tamanu oil or another oil comprising a high content of catechin is used.

When using crushed leaves it is preferred that the crushed green tea leaves have an average dimension of less than 1 mm, preferably in the range of from 1 to 0.05 mm, or example 1 to 0.1 mm. Such yields an excellent absorption of active substances and a long term operation. A dimension of less than 0.05 mm is allowable as well, but in case of oral administration may not yield an improved absorption of active ingredients by the subject that is treated. The maximum absorption by the subject to be treated of the active ingredients may be larger, but the long term activity may be less than the range as mentioned above. Preference is especially given to a dimension of from 1 to 0.05 mm, for example 1 to 0.1 mm. Such provides an optimum catechin from the leaves and a maximum long term absorption into the subject's body.

According to a further aspect the invention relates to a pharmaceutical formulation comprising a composition according the invention and as mentioned above for use in treatment of type I allergy and a suitable carrier. Analogously, the invention relates to a nutritional supplement comprising a composition according to the invention, as especially mentioned in any of claims 12 to 15, in a use for preventing symptoms of type I allergy and a suitable carrier.

It has shown that the combined use of topically and orally with a composition according to the invention for treatment of type I allergy provides an optimum result. The oral administration both provides for recovery from the wounds, especially in case of SME, as a preventive protection against allergic reactions I case of future exposure to allergens. A combination of oral administration and topical use provides for a quick recovery of damages that have already occurred. According to a further aspect, the invention therefore relates to a combination of components for treatment of type I allergy, comprising [I] at least one of a dried extract of green tea leaves and an extract of green tea leaves in oil for topical use, and [II] at least one of a dried extract of green tea leaves and crushed green tea leaves for oral administration.

The examples show the use of green tea and components thereof, like catechin, that is administered to the subject to be tested. The amount of catechin in green tea leaves may amount to about 25% (w/w).

In daily administration the amount of catechin to be administered may preferably be 25-250 mg/kg body weight. The amount of green tea (dry weight) that is required for such amount, and that for example may be administered as crushed leaves, may be about 0.1-1.0 g/kg body weight. The amount of green tea to be administered may be supplemented with for example green tea extract that has a content of catechin of about 85%. As a consequence, the amount of catechin to be administered to a horse may be for example up to 500 mg/kg bodyweight. The amount of green tea that actually is to be administered is dependent on the kind of the an the nature and kind of the leaves.

The amount of green tea that is required for maintaining a result that has already been achieved, may for example be up to 100 mg/kg body weight per week. This conservation dose may advantageously be administered once a week. Such is the case when a horse has been administered the said dose of the composition according to the invention during a couple of years during the SME season (April to October) substantially as a daily dose.

The invention will hereafter be further described with reference to some examples.

Green tea was administered in a variety of ways.

[a] Crushed green tea leaves, enriched with catechin in a ratio of 20 g added catechin per 50 g crushed green tea leaves, were fed dryly to horses. Because of the bitter taste of the added catechin oral administration was difficult for some horses. Admixing mashed apples or solid food increased the horse's appetite for this mixture.

[b] Crushed green tea leaves were mixed with oil with which horses were treated topically. This treatment is only directed to acute treatment of skin that was damaged due to type I allergic reactions. The efficiency seems to be limited to the parts of the skin that was damaged and treated.

EXAMPLE I: PREVENTIVE PROTECTION AGAINST SME

Finely crushed green tea leaves were administered topically daily on some horses that showed symptoms of SME on the damaged skin. The horses treated this way chaffed much less and the damages skin started to heal. After 10 days these horses were administered a daily dose of 40-55 g crushed green tea leaves orally. The average particle size was in the range of from about 0.05-1 mm. The horses were standing outside, effectively unprotected against insects. The treated horses showed substantially less complaints due to SME after a month of treatment in respect with the start of the treatment.

Untreated horses suffering from SME, held on the same meadow, as a control group, were compared with the treated horses and did not receive any green tea leaves.

A horse, the SME symptoms of which had greatly diminished after it had been subjected to the combination of topical treatment and oral treatment, showed after a stop of the oral treatment for a week, again SME symptoms, despite the fact that the topical treatment was continued.

In the control group of untreated horses the SME complaints did not diminish.

The only difference in circumstances between the group of treated horses and the group of untreated horses, was the administration of green tea leaves comprising a high content of catechin.

The treatment therefore has a very positive effect on protection against SME.

EXAMPLE II: TREATMENT OF SME

Figure 4:
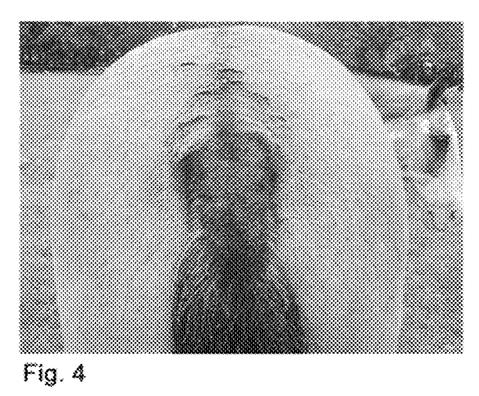
Figure 5:
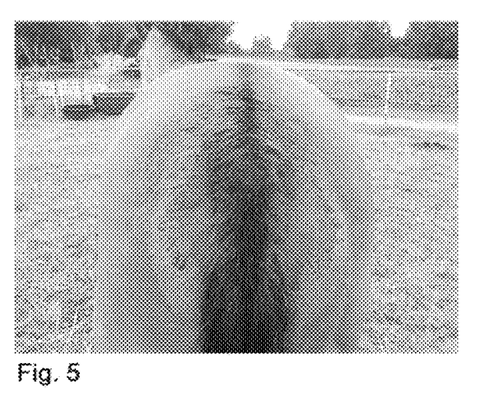

A horse (weight 400 kg) suffering from SME, due to Culicoïdes midgets, had a severely damaged skin due to allergic reactions to the midget's saliva, wherein damaged skin parts varied in diameter between a few centimeters to 45 cm (situation on day 0, FIG. 4). The attachment of the tail was chaffed with all hair disappeared, oedemic (sub skin fluid retention) and showed wounds. Topical administration of a composition of crushed green tea leaves according to the invention in oil provided in combination with oral administration of 40-55 g crushed green tea leaves a quick improvement of the damaged skin. After a few weeks treatment the damaged skin was healed and a new fur started to appear (situation on day 27, FIG. 5). Based on the subject's behavior, it may be concluded that the itch had disappeared within a few days. The damaged skin showed a considerable improvement wherein the damaged skin had remained dry.

The oil used was a mixture of tamanu oil and argan oil in a mutual ratio of 60:40 (vol./vol.). The use in a range of ratios of from 100:0 to 60:40 provides good results. The amount of crushed green tea leaves was about 50 g/horse. To this, an additional 20 g/horse of catechin was added. The amount that was administered topically was sufficient to completely cover the wound, and such that a surplus flowed off from the skin. The oil was administered 1 time a day during three subsequent days.

The extract in oil only should be added to the treated skin as long as said treated skin is wet or carries scabs. Oral administration that was started concurrently with said topical administration of the composition provided for a dramatical reduction of the symptoms, even with continued exposure to midgets.

EXAMPLE III: TREATMENT OF SME

Figure 1:
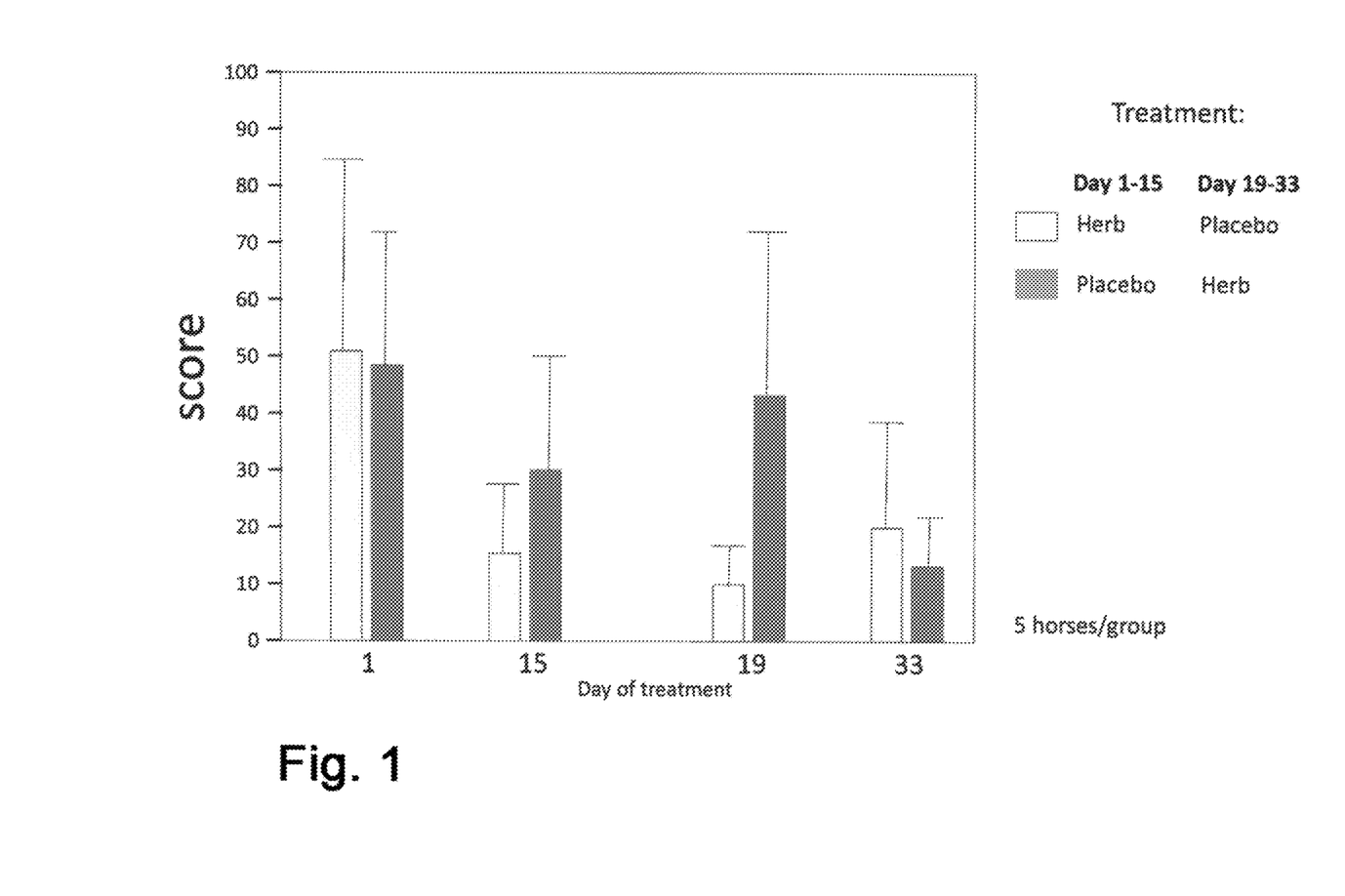
FIGS. 1-5, 6a, 6b, 7a, 7b, and 7c all relate to the Examples relating to the invention as described below.

The graph shows the efficiency of the dried green tea extract (strongly enriched with catechin powder), topically administered as an emulsion in oil, to SME. The active ingredient was administered topically. In this example a topical use (as described before) was combined with oral administration of crushed green tea leaves with additional catechin added.

The placebo consisted of a treatment with oral administration of crushed grass and carotene powder only, with a similar appearance as green tea and dried green tea extract (catechin), respectively.

The oil containing catechin was used during the first 3 days only, after which the treatment was performed with daily administration of tea leaves enriched with catechin.

A first group of horses received during two weeks the active composition according to the invention in a daily routine, whereas a second group during that same time period received a placebo.

After a resting period of 4 days, the administration to both groups was reversed, wherein the first group received said placebo and the second group received the active composition according to the invention.

The results are shown in the graph (FIG. 1).

It can be seen clearly that the active ingredient yielded a profound improvement of the skin damages due to SME (expressed as SME score). The improvement due to the administration of the treatment is remarkably better than the placebo.

The efficiency of the treatment seems to continue after ending the treatment, such that the symptoms of SME 4 days after stopping the treatment (19 in FIG. 1) had not fully returned and also two weeks after the placebo treatment (33 in FIG. 1) still fell behind with respect to the starting situation on day 0. However, the treatment is clearly effective during the second time period in the group that was treated during said second time period with green tea and catechin (FIG. 1: day 19-33, herb). The SME score strongly diminishes with respect to the previous measuring points (day 1, 15 and 19) as this group of horses had been treated with the placebo. As a consequence, it may be concluded that the topical and oral treatment provide a strong improvement of the symptoms.

EXAMPLE IV: TREATMENT OF MOK

A horse with a severely damaged skin above its hoof, commonly known as mud fever, was treated with the use according to the invention. Mud fever may amongst others be due to insects.

Figure 2:
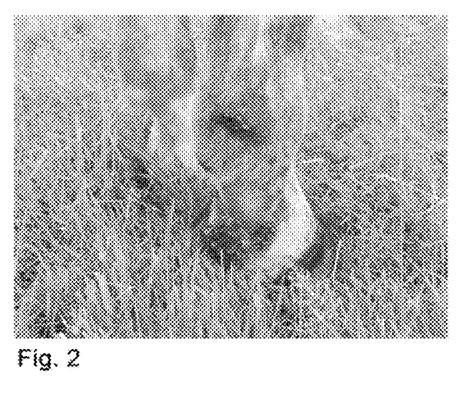

The skin that was affected by mud fever (starting situation at day 0 as shown in FIG. 2) was treated topically according to the invention with a composition comprising crushed green tea leaves and supplemented with green tea extract.

Figure 3:
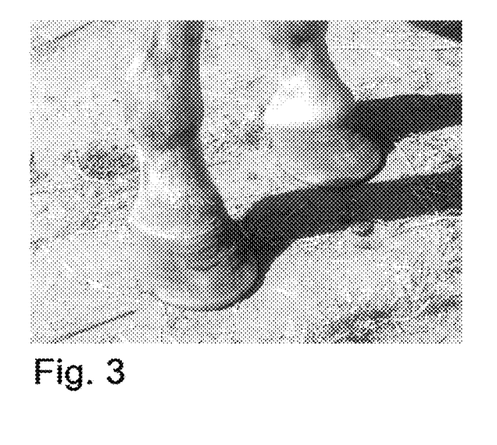

Topical administration of a composition of crushed green tea leaves according to the invention in oil in combination with oral administration of 40-55 g crushed green tea leaves provided a quick improvement of the damaged skin. After about 4 weeks of treatment the affected skin healed and started to grow new hairs (situation on day 27, FIG. 3). Based on the treated subject's behavior, it may be concluded that the itch disappears within a few days. The affected skin showed a considerable improvement after only two days wherein the damaged skin had become dry.

The oil used was a mixture of tamanu oil and argan oil in a ratio of 60:40 (vol./vol.). The use in a range of ratios of from 100:0 to 60:40 provides good results. The amount of crushed green tea leaves was about 50 g/subject/day. To this, some catechin was added in an amount of 20 g/subject/day. The amount of that was administered topically was sufficient to completely cover the wound, and was such that a surplus flowed off of the wound. The oil was administered 1 time a day during three subsequent days.

The extract in oil was administered to the damaged skin only as long as said skin was wet or had crabs. Oral administration was started concurrently with topical administration of the composition which dramatically reduced the symptoms.

The horse being the subject of these tests also suffered from summer eczema, disappearing concurrently with the mud fever, despite a continuous exposure to midgets.

EXAMPLE V: LONG TERM EFFECT

A mare of six years (weight: 400 kg) had a severe form of sweet itch (SME) with the affected pieces skin all over the body. All wounds and inflamed spots were topically treated one time with green tea. The affected spots were fully covered with a powdered substance of green tea soaked in oil (a mixture of Tamanu:argan=60:40 vol./vol.). The spots that were affected most severely (especially at the tail and mane) were treated once a day at three consecutive days. Within four days the skin was much improved (less inflamed). The affected skin comprised dozens of spots with a diameter of 0.5 to 4 cm, each. Then, during seven days no treatment of the affected spots was performed. Although the skin was less inflamed after these seven days, the SME symptoms had not fully disappeared. For that reason, ten days after starting the topical treatment (that is to say, seven days after the last topical treatment) a daily dose of green tea was administered orally (100 gram each day). One week after the start of this oral treatment the horse did not chaff anymore and seemed to be free of itch. Topical treatment was limited to the first three days.

The horse was fed a daily dose of green tea in an amount of 100 gram, during the first year from end of May to mid-October (in 2012). During this period the horse did not suffer from itch (the treatment was performed in the Netherlands, where the temperature is too low from mid-October for midgets which then are not or much less active).

During the second year (2013) preceding the start of the midget season, starting somewhere mid-April, a start was made with administering about 75 gram green tea a day. The horse remained outside during day and night. That year, there was a stop for two times in feeding the green tea (1× during 2 weeks (mid-July) and 1× during 4 weeks (in August)), after which the SME complaints returned. The remaining art of the summer and autumn until the end of the season (start of October) The horse was administered a daily dose of 50 gram green tea each day, after which the SME complaints disappeared and did not return.

In the third year (2014, from May until September) the horse was administered once every ten days a dose of 50 gram green tea; no SME symptoms were noticed. Even after the midgets returned in the fourth year in May, the SME complaints did not return.

In the fourth year the horse was completely void of SME complaints, even without administering green tea. The horse is not protected against midgets by means of insect blankets or insect sprays or similar.

Figure 6A:
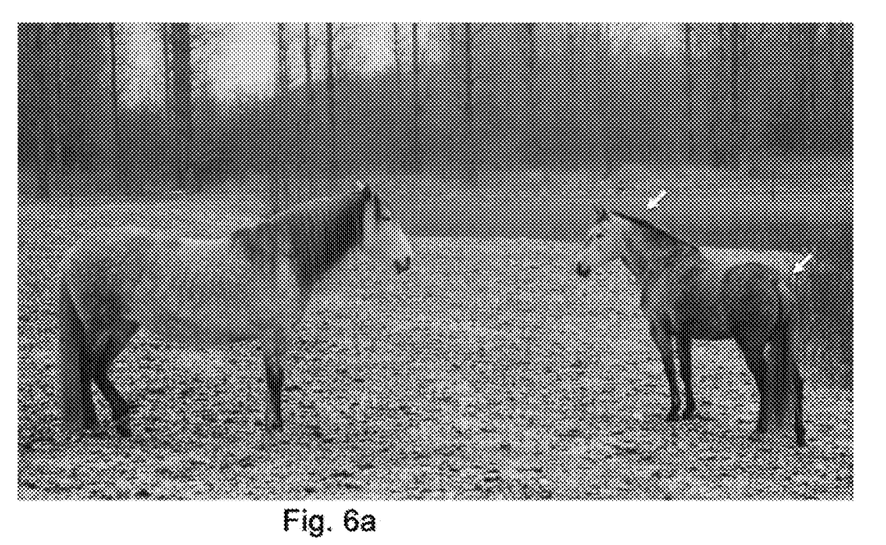
Figure 6B:
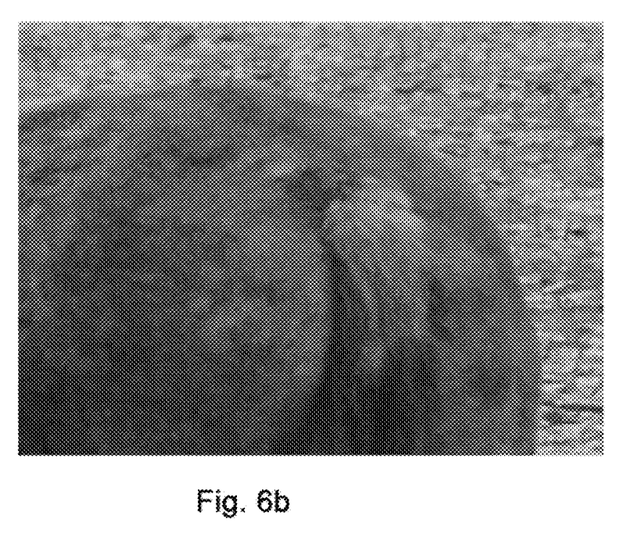
Figure 7A:
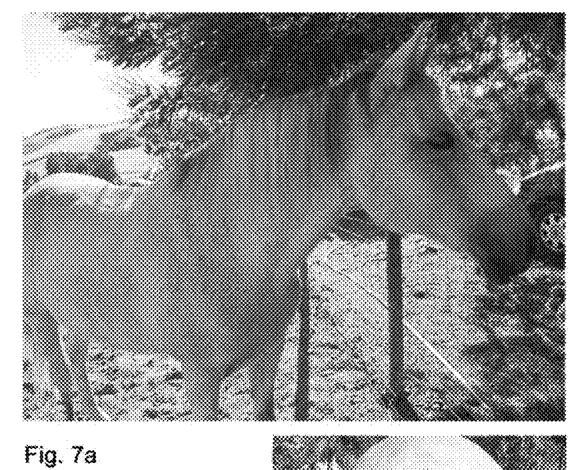
Figures 7B, 7C:
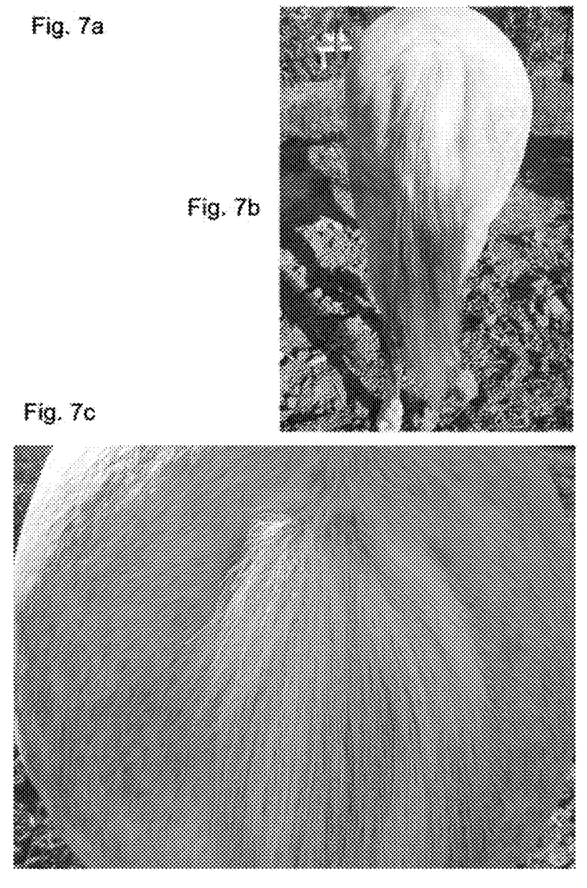

Pictures of FIGS. 6a and 6b of this horse show the symptoms before treatment (situation May 2012). Pictures in FIG. 7a, 7b, 7c show the long term effect of the green tea treatment. The pictures were taken before commencing the treatment (FIGS. 6a and 6b) and show that the manes have disappeared due to chaffing and that the upper part of the tail and the skin around the tail attachment has chaffing spots. The skin is severely irritated.

FIGS. 7a, 7b and 7c show pictures taken in September 2015 and showing that the manes of the horse have fully recovered and that the hair at and near the tail has fully recovered since the horse did not chaff anymore. After having been treated during a few years during the midge season (from May to October, wherein the temperature is at least 15° C.) with green tea, sweet itch (SME) symptoms have fully disappeared. Also, during the midget season of the subsequent year the symptoms did not return. That year, no treatment against SME was performed at all, not with green tea and neither in any other way, being an indication of a surprising long term effect and probably even a curing effect of green tea treatment for this allergic disease.

The invention is not limited to the examples described above and as shown in the embodiments. The invention is limited only by the appending claims.

The invention also embodies all combination of features that have been described in this description independently from each other.

What is claimed is:

1. A veterinary method of treating sweet itch, the method comprising:
    administering a composition of crushed leaves of green tea to the veterinary animal suffering from sweet itch, said administration includes oral administration, or a combination of a topical treatment and oral administration wherein said oral administration is an oral dose of green tea in an amount in the range of from 0.1 to 1.0 gram per kg weight of the subject to be treated.

2. The method according to claim 1, wherein said composition is supplemented with substances extracted from green tea.

3. The method according to claim 2, wherein said composition is supplemented with catechin or a derivative thereof.

4. The method according to claim 1, comprising the step of covering skin that has been affected by sweet itch with crushed leaves of green tea.

5. The method according to claim 4, comprising the step of covering skin that has been affected by sweet itch with a mixture of crushed leaves of green tea and oil.

6. The method according to claim 5, comprising the step of covering skin that has been affected by sweet itch with a mixture of crushed leaves of green tea and at least one of argan oil and tamanu oil.

7. The method according to claim 1, comprising daily administration of an oral dose of green tea in an amount in the range of from 0.1 to 1.0 gram per kg weight of the subject to be treated.

8. The method according to claim 7, comprising daily administration of an oral dose of green tea in an amount in the range of from 0.1 to 0.75 gram per kg weight of the subject to be treated.

9. The method according to claim 8, comprising daily administration of an oral dose of green tea in an amount in the range of from 0.1 to 0.5 gram per kg of the subject to be treated.

10. The method according to claim 1, wherein the composition comprises at least one of: [a] a dried extract of green tea leaves, [b] a dried extract of green tea leaves in oil, and [c] crushed green tea leaves in oil.

11. The method according to claim 10, wherein said crushed green tea leaves have an average particle size in the range of from 1 mm to 0.05 mm.

12. The method according to claim 1, said crushed green tea leaves being enriched with catechin.

13. The method according to claim 1 further comprising orally administering during at least two months of a first season an amount of a substantially daily dose of green tea in an amount in the range of from 0.1 to 1.0 gram per kg weight of the subject to be treated; and
    orally administering during a second season an amount of a substantially daily dose of green tea in an amount in the range of from 0.1 to 1.0 gram per kg weight of the subject to be treated.

14. The method according to claim 13, wherein one or both administering steps are applied during a time period wherein ambient temperature is above 15° C.

15. The method according to claim 13, additionally comprising orally administering during a third season, for every unit of time of 1 day to 14 days, an amount of an oral dose of green tea in an amount in the range of from 0.05 to 0.75 gram per kg weight of the subject to be treated.

\* \* \* \* \*